United States Patent [19]

Ohachi

[11] Patent Number: 4,657,542
[45] Date of Patent: Apr. 14, 1987

[54] MEDICAL INSTRUMENT USED FOR STORAGE OF BLOOD

[75] Inventor: Yoshinori Ohachi, Fujinomiya, Japan

[73] Assignee: Terumo Kabushiki Kaisha, Tokyo, Japan

[21] Appl. No.: 695,052

[22] Filed: Jan. 25, 1985

[30] Foreign Application Priority Data

Feb. 2, 1984 [JP] Japan .................................. 59-17621

[51] Int. Cl.⁴ ............................................. A61B 19/00
[52] U.S. Cl. ..................................... 604/410; 523/105; 524/114; 524/296; 524/297; 604/4; 604/5; 604/6; 604/262; 604/408; 604/409
[58] Field of Search ........................................ 604/4–6, 604/262, 408, 409, 410; 523/105; 524/114, 296, 297

[56] References Cited

U.S. PATENT DOCUMENTS

| | | | |
|---|---|---|---|
| 3,940,802 | 3/1976 | Sako et al. | 523/105 X |
| 4,082,711 | 4/1978 | Andrascheck et al. | 524/114 |
| 4,193,898 | 3/1980 | Miller | 524/114 |
| 4,300,559 | 11/1981 | Gajewski et al. | 604/262 X |
| 4,451,259 | 5/1984 | Geissler et al. | 524/297 X |
| 4,478,961 | 10/1984 | Tanaka et al. | 523/105 |
| 4,495,312 | 1/1985 | Hata et al. | 523/105 |

FOREIGN PATENT DOCUMENTS

| | | |
|---|---|---|
| 0054221 | 6/1982 | European Pat. Off. . |
| 0057470 | 11/1982 | European Pat. Off. . |
| 0095526 | 12/1983 | European Pat. Off. . |
| 3318875 | 11/1984 | Fed. Rep. of Germany . |
| 2542320 | 9/1984 | France . |
| 59-164066 | 9/1984 | Japan . |
| 59-189858 | 10/1984 | Japan . |
| 875999 | 8/1961 | United Kingdom . |
| 1301312 | 12/1972 | United Kingdom . |
| 1447853 | 9/1976 | United Kingdom . |
| 2017112 | 10/1979 | United Kingdom . |
| 2139231 | 11/1984 | United Kingdom . |

Primary Examiner—Lucille M. Phynes
Attorney, Agent, or Firm—Frishauf, Holtz, Goodman & Woodward

[57] ABSTRACT

A medical instrument is disclosed which is a shaped article of a resin composition comprising 100 parts by weight of a vinyl chloride type resin, 10 to 80 parts by weight of a di-n-alkyl ester of phthalic acid whose alkyl groups each possess 8 to 14 carbon atoms and whose numbers of carbon atoms in said alkyl groups average 9 to 14, and 1 to 18 parts by weight of a stabilizer. The medical instrument exudes only an extremely small amount of plasticizer and excels in permeability to gas.

17 Claims, 1 Drawing Figure

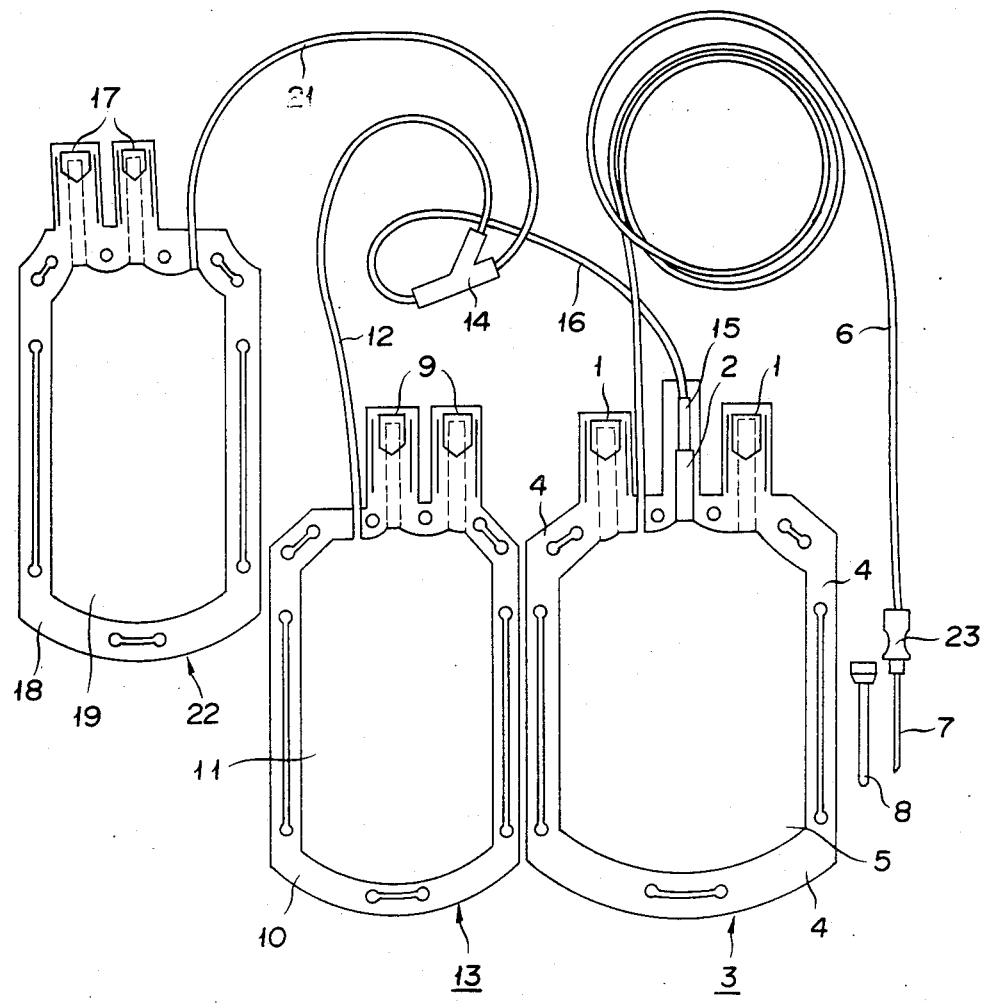

MEDICAL INSTRUMENT USED FOR STORAGE OF BLOOD

BACKGROUND OF THE INVENTION

1. Field of the Invention

This invention relates to a novel medical instrument. More particularly, this invention relates to a medical instrument which exudes plasticizer only in an extremely small amount and exels in permeability to gas.

2. Description of Prior Art

The blood, as widely known, has a self-protective function. On contact with a boundary other than the inner wall of the blood vessel, the blood induces adhesion and aggregate of blood platelets and gelation of blood plasma, namely formation of fibrin cross-links, on the extraneous boundary. In the conventional blood bag, blood platelets in the blood aggregate on the boundary of the plastic material of the blood bag so that the ability of blood platelets to aggregate falls, in 6 hours after blood collection, to about 60% and, in 24 hours similarly, to about 40% respectively of the original level existing at the time of blood collection. For the sake of effective use of existing blood platelet preparations, the desirability of developing plastic preserving containers capable of preserving blood for longer periods of time, plastic preserving containers possessed of what is called blood adaptability, or other similar medical instruments, has been winning popoular approval. At present, such plastic containers or other plastic medical instruments which are made of flexible vinyl chloride resin are widely used because they are desirable in terms of fabricability, flexibility, transparency, water vapor permeability and resistance to heat. These articles of flexible vinyl chloride resin contain di-2-ethylhexyl phthalate (hereinafter referred to as DOP) and other phthalic esters in proportions of 30 to 60 parts by weight as plasticizer. It is known that since phthalic esters have a high migrating property, in blood preserving containers made of such flexible vinyl chloride resin, these phthalic esters exude from the walls of the containers and mingle into blood plasma. It has been reported that when a phthalic ester exude into blood plasma containing concentrated blood platelets, it brings about a decline in the aggregation ability of blood platelets [Journal of Japan Blood Transfusion Study Society, 28, 282 (1982)]. The flexible vinyl chloride resin which contains any of the aforementioned phthalic ester type plasticizer does not possess sufficient permeability to gas and the period during which the blood bag made of this resin exhibits the blood platelet preserving property is generally as short as six hours (according to Service Standard of Red Cross Blood Center, the Japan Red Cross Society). It has been known that the blood bag excels in ability to preserve blood corpuscles and blood platelets when it has high permeability to gas [(1) "Platelet Concentrations Stored at 22° C. Need Oxygen"; Jonas Wallvik, Olof Åkerblom; Vox. Sang. 45, 303–311 (1983), (2) "On Effects of Permeability of Container to Gas Manifested on Partial Pressure of Gas and Function of Preserved Blood", Uehira et al., Glossary of Manuscripts published at the 31st General Meeting of Japan Blood Transfusion Study Society, P 101 (1983)]. Thus, when the amount of the plasticizer such as DOP to be contained is increased, the permeability of the blood bag to gas is improved and the mechanical strength thereof is lowered. When the amount of the plasticizer is increased, the exudation of the plasticizer into the blood plasma is increased and, consequently, the preservability of blood platelets is greatly impaired.

For the purpose of enhancing the preservability of blood platelets, incorporation of tri-2-ethylhexyl trimellitate (TOTM) in flexible vinyl chloride resin as a plasticizer has been proposed (U.S. Pat. No. 4,280,497). TOTM, however, has the disadvantage that it is extremely deficient in plasticizing efficiency and permeability to gas besides being extremely expensive.

In the fabrication of blood bag from a plastic sheet, for example, when the thickness of the film is in the range of 300 to 400 μm, the generally accepted indispensable limits in repressing the permeation of water, the permeability to gas which permits long preservation of blood corpuscles and blood platelets, i.e. the permeability coefficient of not less than $2.5 \times 10^3$ ml·mm/m²·day·atm (30° C.), preferably not less than $3.0 \times 10^3$ mm·mm/m²·day·atm (30° C.), with respect to carbon dioxide gas, is difficult to obtain.

Polyester type plasticizers are used as plasticizers of the non-migrating type. It is well known, however, that since these polyester type plasticizers are generally formed preponderantly of fatty esters, they are inferior to phthalic esters having phenyl groups as the chain thereof in terms of resistance to water and resistance to hydrolysis. Further, these plasticizers generally possess high molecular weights and, therefore, exhibit low permeability to gases.

As a material for blood bag which exhibits rather desirable permeability to gases, a resin composition comprising a blend of 10 to 40% by weight of polypropylene and 40 to 85% by weight of a thermoplastic elastomer has been known to the art (Japanese Patent Application Laid-open No. SHO 55(1980)–60464). Polyolefin type resins possess inferior adhesiveness and, therefore, cannot be fused easily with the high-frequency welder during the second fabrication and do not permit free selection of any desired molding method. They are further destitute of the flexibility possessed by flexible polyvinyl chloride resin.

An object of the present invention, therefore, to provide a novel medical instrument. Another object of this invention is to provide a medical instrument which exudes very little plasticizer and excels in permeability to gas.

SUMMARY OF THE INVENTION

The objects described above are attained by a medical instrument molded with a resin composition comprising 100 parts by weight of vinyl chloride type resin, 10 to 80 parts by weight of a di-n-alkyl ester of phthalic acid possessing the general formula I:

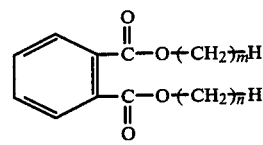

[I]

wherein m and n each denotes an integer of the value of 8 to 14 and (m+n)/2 has a value of 9 to 14, and 1 to 18 parts by weight of a stabilizer.

This invention is also directed to a medical instrument having 9 to 12 carbon atoms in a straight-chain alkyl group thereof. This invention is further directed to a medical instrument having di-n-decylphthalate as the di-n-alkyl ester of phthalic acid. This invention is directed further to a medical instrument comprising 100 parts by weight of vinyl chloride type resin, 10 to 70 parts by weight of the di-n-alkyl ester of phthalic acid possessing the general formula I, and 2 to 15 parts by weight of a stabilizer. Further this invention is directed to a medical instrument having an epoxidized vegetable oil and a calcium-zinc type stabilizer as principal components of the stabilizer therefor. The medical instrument of the present invention is a blood bag. This invention is directed to a medical instrument which exudes the di-n-alkyl ester of phthalic acid in only a very little amount. This invention is further directed to a medical container which has a permeability coefficient of $2.5 \times 10^3$ ml·mm/m$^2$·day·atm (30° C.) with respect to carbon dioxide gas.

BRIEF DESCRIPTION OF THE DRAWING

The drawing is a front view illustrating a typical medical instrument embodying the present invention.

DESCRIPTION OF PREFERRED EMBODIMENT

As the vinyl chloride type resin for use in the resin composition of the medical instrument of the present invention, not only homopolymer of vinyl chloride but also polyvinylidene chloride or a copolymer of not less than 70% by weight, preferably not less than 85% by weight, of vinyl chloride with another monomer copolymerizable therewith is desirably used. The average polymerization degree of the vinyl chloride type resin is in the range of 700 to 3,000, preferably 1,000 to 2,400. Examples of the comonomer for vinyl chloride include vinylidene chloride, ethylene, propylene, vinyl acetate, vinyl bromide, vinyl fluoride, styrene, vinyl toluene, vinyl pyridine, acrylic acid, alkyl acrylates (such as methyl acrylate, ethyl acrylate, isopropyl acrylate, n-butyl acrylate and l-ethylhexyl acrylate), methacrylic acid, alkyl methacrylates (such as methyl methacrylate, ethyl methacrylate and 2-ethylhexyl methacrylate), acrylonitrile and methacrylonitrile. The vinyl chloride resin can incorporate therein styrene-acrylonitrile copolymer or styrene-methacrylonitrile copolymer.

The di-n-alkyl ester of phthalic acid usable as the plasticizer is represented by the general formula I. It is used in an amount of 10 to 80 parts by weight, desirably 40 to 70 parts by weight, and more desirably 50 to 60 parts by weight, based on 100 parts by weight of the vinyl chloride type resin. In the general formula, m and n each have a value of 8 to 14, desirably 9 to 12, and most desirably 10, and (m+n)/2 has a value of 9 to 14. If the number of carbon atoms is not more than 7, the produced medical instrument exudes the plasticizer in a large volume. If the number of carbon atoms exceeds 15, the alkyl ester possesses insufficient plasticizing efficiency and must be incorporated in an excessive amount to confer ample flexibility to the resin composition. The alkyl ester used in an excessive amount is inferior in compatibility with the vinyl chloride type resin and increases the permeability to steam. It has been ascertained, surprisingly, to the inventors that the aforementioned alkyl group, when possessing a branched chain, is incapable of conferring ample permeability to gas upon the resin composition and that the permeability to gas is high only when the alkyl group is in the form of a straight chain.

Examples of the di-n-alkyl ester of phthalic acid possessing the aforementioned general formula I include di-n-nonyl phthalate, di-n-decyl phthalate, di-n-undecyl phthalate, di-n-dodecyl phthalate, di-n-tridecyl phthalate, n-octyl-n-decyl phthalate, n-decyl-n-tridecyl phthalate, and mixtures thereof. Besides the aforementioned di-n-alkyl ester of phthalic acid, the resin composition of the present invention may incorporate some other plasticizer in an amount not departing from the range in which the attainment of the objects of this invention is not jeopardized.

Examples of the stabilizer are at least one epoxy compound such as an epoxidized vegetable oil represented by epoxidized soybean oil and epoxidized linseed oil and cyclohexene oxide derivatives represented by di-2-ethylhexyl-epoxyhexahydrophthalate, vinyl cyclohexene dioxide, 3,4-epoxy-6-methylcyclohexyl-methyl-3,4-epoxy-6-methylcyclohexane carbonate, and dicyclopentadiene dioxide, at least one metallic soap of calcium, zinc, barium, magnesium, tin, etc. and stearic acid, lauric acid, ricinolic acid, naphthenic acid, 2-ethylhexoinic acid, etc. represented by calcium stearate, zinc stearate, calcium laurate, zinc laurate, barium stearate, magnesium stearate, and tin stearate, and mixtures between the aforementioned epoxy compound and the aforementioned metallic soaps. Besides these, stabilizers such as a phosphorous ester represented by didecylphenyl phosphite and an another organic stabilizer such as a mixture between stearoyl benzomethane and palmitoylbenzoyl methane are other examples. The amount of the stabilizer to be used generally falls in the range of 1 to 18 parts by weight and preferably in the range of 2 to 15 parts by weight, based on 100 parts by weight of the vinyl chloride type resin. The aforementioned stabilizers are usable singly. It is, however, desirable to use the aforementioned epoxy compound in combination with the metallic soap, phosphorous ester or organic stabilizer. The epoxy compound mentioned above is used generally in the range of 1 to 15 parts by weight, preferably in the range of 5 to 10 parts by weight, based on 100 parts by weight of the vinyl chloride type resin. Epoxidized soybean oil is preferred over all the other epoxy compounds. The metallic soap, phosphorus ester, or organic stabilizer is used generally in the range of 0.01 to 8 parts by weight, based on 100 parts by weight of the vinyl chloride type resin. Ca-Zn type metallic soaps are preferred over the other stabilizers of the mentioned above.

Now, a blood collection bag produced as a typical medical instrument of the present invention will be described below with reference to the accompanying drawing. The drawing illustrate the blood collection bag. The blood collection bag 3 made of the resin composition of this invention and provided with a plurality of discharge outlets 1 fitted with a peel tab and a discharge outlet 2 has the peripheral edge thereof fused by high-frequency heating or some other suitable heating means. A blood collection tube 6 made of the resin composition of this invention and adapted to communicate with an inner space 5 of the blood collection bag is connected thereto. This blood collection bag contains in the inner space thereof, as an anticoagulant, ACD-A solution (containing 2.20 g of sodium citrate, 0.80 g of citric acid and 2.20 g of glucose in 100 ml of aqueous solution, for example) or CPD solution (containing 0.327 g of citric acid, 0.251 g of sodium dihydrogenphosphate, and dextrose in 100 ml aqueous solution). To the leading end of the aforementioned blood collection tube 6 is attached a blood collection needle 7. This blood collection needle is provided with a cap 8.

When aforementioned blood collection bag 3 is required to have satellite bags made of the resin composition of the present invention appended thereto, a first satellite bag 13 provided with access ports 9 fitted with a peel tab, having the peripheral edge 10 thereof fused, and provided with a connection tube 12 of the resin composition of this invention communicating with the inner space 11 is connected via a branching tube 14 to a connection tube 16 which in turn is connected to the connection discharge outlet 2 of the blood collection bag 3 through the medium of a connecting part disposed 15 at the leading end of the discharge outlet 2. Further, a satellite bag 22 provided with access ports 17 fitted with a peel tab, having the peripheral boundary thereof 18 fused by means of high-frequency welder, and provided with a connection tube 21 of the resin composition of the present invention communicating with an inner space 19 thereof has the aforementioned connection tube 21 connected via the branching tube 14 to the connection tubes 12, 16.

The medical instrument of the present invention has been described as embodied in the form of a blood bag. It can also be embodied in blood preserving containers, containers for blood transfusion system, containers for blood circulation system, bags for transfusion fluids, various medical tubes represented by catheters and cialytic tubes, artificial organs including artificial kidney, artificial lung, and artificial liver, and tubes for respiratory ducts and other tools relating to respiratory ducts. In the case of the tube for a respiratory duct adapted to pass a heated gas from the ventilator side, when the tube is made of the resin composition of the present invention, the possibility of plasticizer being vaporized into the gas and inhaled into the human body as experienced when the tube is made of the conventional resin composition is precluded. The medical instrument of the present invention manifests its effect conspicuously when it is used in the blood bag and in the tube connected to the bag. Essentially, it is suitable for applications in which liquids and gases such as body fluids and medicinal solutions are introduced, discharged, preserved, or brought into contact. All these applications are satisfied by the present invention and are not discriminated by function.

Now, the present invention will be described more specifically below with reference to working examples.

Examples 1–4 and Controls 1–7

By mixing 100 parts by weight of polyvinyl chloride (average polymerization degree 1,300) with varying numbers of parts by weight of plasticizer and stabilizer indicated in Table 1 and by extrusion molding the resultant mixture, a sheet about 0.4 mm in thickness was obtained. Two pieces of a stated size were cut from the sheet and superposed one over the other. By fusing the peripheral boundary of the superposed pieces by high-frequency sealing to produce an experimental blood bag having an inner surface area of about 50 cm$^2$. The bag, with the opening sealed by fusing, was sterilized with high-pressure steam (by autoclaving). The bags of Examples 1–4 were not found to sustain any discernible deformation due to heat.

Three such bags were prepared for each example and each control, each charged with 5 ml of CPD-added blood plasma sterilely, sealed, and then left standing in an oven at 37° C. for 24 hours. After standing, the portions of blood plasma were removed from the bags and tested for the amount of plasticizer exuded into the plasma, with the found values averaged and reported. The results are shown in Table 1. By this procedure, the bags were tried on bovine blood plasma to determine the amount of plasticizer exuded in the blood plasma. The bags were further tested for various properties. The results are also shown in Table 1.

TABLE 1

| Example | Control 1 | Control 2 | Control 3 | Example 1 | Control 4 | Control 5 |
|---|---|---|---|---|---|---|
| Kind of plasticizer | DOP | TOTM | DnOP | DnDP | DnDP | DnDP |
| Amount of plasticizer (phr) | 52 | 52 | 52 | 52 | 40 | 30 |
| Amount of epoxidized soybean oil (phr) | 8 | 8 | 8 | 8 | 21 | 32 |
| Amount of Ca—Zn type stabilizer (phr) | 0.1 | 0.1 | 0.1 | 0.1 | 0.1 | 0.1 |
| Amount exuded in human blood plasma (μg/ml) | 238 | 0.3 | 151 | 10 | | |
| Amount exuded in bovine blood plasma (μg/ml) | 146 | | | | 0.5 | 0.5 |
| Initial elastic modulus (kg/mm$^2$) (at 23° C.) | 0.80 | 1.34 | 0.59 | 0.81 | 1.30 | 0.65 |
| 100% Modulus (kg/cm$^2$) (at 23° C.) | 92 | 110 | 71 | 84 | 95 | 87 |
| Tensile strength (kg/cm$^2$) (at 23° C.) | 219 | 224 | 193 | 200 | 216 | 197 |
| Extraction test | | | | | | |
| ΔpH | 0.70 | 0.53 | 0.45 | 0.95 | 0.96 | 1.08 |
| ΔKMnO$_4$ | 0.40 | 3.93 | 0.33 | 0.13 | 1.10 | 1.47 |
| Ultraviolet absorption | | | | | | |
| (220 nm) | 0.057 | 0.635 | 0.060 | 0.040 | 0.184 | 0.316 |
| (241 nm) | 0.020 | 0.073 | 0.033 | 0.023 | 0.077 | 0.133 |
| Test for hemolytic toxicity | — | — | — | — | — | — |
| Test for cytotoxin | — | — | — | — | — | — |
| Permeability to CO$_2$* | 1.00 | 0.83 | 1.61 | 1.66 | 1.43 | 1.22 |
| Water vapor permeability* | 1.00 | 1.01 | 1.02 | 1.14 | 1.14 | 1.13 |

| Example | Example 2 | Control 6 | Control 7 | Example 3 | Example 4 |
|---|---|---|---|---|---|
| Kind of plasticizer | A | TITM | DTDP | DLP | DnDP + DLP |
| Amount of plasticizer (phr) | 52 | 52 | 52 | 52 | 30 + 30 |
| Amount of epoxidized soybean oil (phr) | 8 | 8 | 8 | 8 | 8 |
| Amount of Ca—Zn type stabilizer (phr) | 0.1 | 0.1 | 0.1 | 0.1 | 0.1 |
| Amount exuded in human blood plasma (μg/ml) | 8 1(DnDP) | 2 | <1 | <1 | <1(DLP), 1(DnDP) |
| Amount exuded in bovine blood plasma (μg/ml) | 5 | 0–1.9 | <1 | <1 | <1(DLP), 1(DnDP) |

TABLE 1-continued

| | | | | | |
|---|---|---|---|---|---|
| Initial elastic modulus (kg/mm$^2$) (at 23° C.) | 1.48 | 4.15 | 2.46 | 2.76 | 1.06 |
| 100% Modulus (kg/cm$^2$) (at 23° C.) | 98 | 128 | 121 | 107 | 85 |
| Tensile strength (kg/cm$^2$) (at 23° C.) | 177 | 215 | 196 | 192 | 176 |
| Extraction test | | | | | |
| ΔpH | 0.85 | 0.63 | 1.29 | 0.33 | 0.24 |
| ΔKMnO$_4$ | 0.61 | 11.5 | 1.38 | 0.35 | 0.38 |
| Ultraviolet absorption | | | | | |
| (220 nm) | 0.099 | >1.0 | 0.197 | 0.040 | 0.047 |
| (241 nm) | 0.041 | 0.180 | 0.101 | 0.024 | 0.028 |
| Test for hemolytic toxicity | — | — | — | — | — |
| Test for cytotoxin | — | — | — | — | — |
| Permeability to CO$_2$* | 1.70 | 0.86 | 0.94 | 1.82 | 1.70 |
| Water vapor permeability* | 1.20 | 1.00 | 1.03 | 1.11 | 1.29 |

DOP: Di-2-ethylhexyl phthalate
TOTM: Tri-2-ethylhexyl trimellitate
DnOP: Di-n-octyl phthalate
DnDP: Di-n-decyl phthalate
*The values given here are relative values with the results of Control 1 taken as 1.00.
DLP: Di-lauryl phthalate
DTDP: Di-tridecyl phthalate
TITM: Triisodecyl trimellitate
DnDP: Di-n-decyl phthalate
A: Mixture of di-n-decyl phthalate, n-decyl-n-dodecyl phthaltate, and di-n-dodecyl phthalate, wherein alkyl group content ratio between n-decyl and n-dodecyl is 6:4.

The tests indicated in the table above were carried out by the following methods.

Test for ΔpH, ΔKMnO$_4$ and ultraviolet absorption:

The method described under the title "Method of testing plastic container for transfusion," B-302 to 318, in the Annotation on the Japanese Pharmacopoeia, Edition 10 was used.

Test for hemolytic toxicity:

The method described under the title "Method of testing plastic container for transfusion," B-305 (1) "Test for hemolytic toxicity" in the Annotation on the Japanese Pharmacopoeia, Edition 10 was used (—: negative, +: positive).

Test for cytotoxicity:

A 1 g of sliced sample was placed in 3 ml of an extracting medium (MEM) culture made by Nissui Pharmaceutical Co., subjected to extraction at 121° C. for 20 minutes, diluted with extracting medium, and inoculated with cells (HeLa-S3). On the following day, and the day after that, the medium was observed under a microscope to determine deformation, excoriation, and impeded growth of cells as compared with controls. The rating of toxicity was made based on the results of observation of the same taken on the second day. (The results were rated on the two-point scale, wherein — stands for satisfactory growth equal to control and + for discernible deformation or impeded growth.)

Test for permeability to carbon dioxide gas:

This test was carried out with a gas permeability tester (L-100) made by Lyssy, at 30° C.

Test for water vapor permeability:

This test was carried out with a vapor permieability tester (L-80) made by Lyssy, at 90% RH.

Example 5 and Control 8

Blood bags having an inner surface area of about 15 cm$^2$ were produced by following the procedures of Examples 1 and Control 1 and using the resin compositions obtained respectively therein. The blood bags were sterilized with high-pressure steam, charged sterilely with about 6 ml of a concentrated blood platelet solution prepared to have about 1,000,000 blood platelets per mm$^3$, and left shaken at room temperature.

The samples of blood platelet solution taken before charging, and 24 hours and 72 hours after the charging were tested for number of blood platelets, blood paltelet non-osmotic pressure resistance (hereinafter referred to as "%HSR"), blood platelet aggregation capacity, $P_{CO2}$ and $P_{O2}$. The results were as shown in Table 2.

TABLE 2

| Example | Bag | Time of sampling | Number of blood platelets[1] | pH | $P_{CO2}$[2] | $P_{O2}$[3] | % HSR | Aggregation of blood platelets (%) |
|---|---|---|---|---|---|---|---|---|
| Example 5 | Example 1 | Before charging | 10.7 × 10$^5$ | 7.11 | 55 | 120 | 78 | 83 |
| | | 24 hrs after charging | 10.1 × 10$^5$ | 7.47 | 16 | 141 | 62 | 32 |
| | | 72 hrs after charging | 10.1 × 10$^5$ | 7.17 | 8 | 148 | 45 | 37 |
| Control 8 | Control 1 | 24 hrs after charging | 9.9 × 10$^5$ | 7.38 | 22 | 131 | 55 | 23 |
| | | 72 hrs after charging | 8.5 × 10$^5$ | 6.70 | 18 | 140 | 16 | 23 |

[1]Unit (number for platelets/mm$^2$)
[2]and [3]Unit (mmHg)
Permeability coefficient to carbon dioxide gas (Example 5): 3.7 × 10$^3$ ml · mm/m$^2$ · day · atm (amount of carbon dioxide allowed to permeate 9.7 × 10$^3$ ml/m$^2$ · day · atm)
Permeability coefficient to carbon dioxide gas (Control 8): 2.2 × 10$^3$ ml/mm/m$^2$ · day · atm (amount of carbon dioxide allowed to permeate 5.8 × 10$^3$ ml/m$^2$ · day · atm)

The tests indicated in Table 2 were carried out by the following methods.

Test for number of blood platelets:

This test was carried out by the use of an automatic blood corpuscle counter, ELT-8 made by OrthoInstrument Corp.

Test for pH, $P_{CO2}$ and $P_{O2}$:

The first sample was taken from the platelet-rich blood plasma freshly prepared by centrifuging CPD whole blood and the samples after 24 hours' and 72 hours' standing were taken from the bags after the concentrated blood platelet solutions contained therein had been intimately stirred and the bags unsealed. The samples, each about 0.5 ml in volume, were collected in insulin injecting syringes, with the syringes tightly sealed by piercing their tips into rubber stoppers. The samples were immediately placed in ice water and preserved there until test. The test was carried out by the use of a blood gas analyzer BK3-MK2, PHM73, made by Radiometer Corp.

Test for blood platelet low osmotic pressure resistance:

By following the method proposed by Valeri et al. and using a platelet-rich blood plasma prepared to have $30 \times 10^4$ blood platelets per $mm^3$, the bags were exposed to osmotic pressure between equal tension and $\frac{2}{3}$ tension at a wavelength of 610 nm for 10 minutes, to determine any change is resistance to the osmotic pressure. The measurement was made by the use of an autospectrophotometer, UV-300, made by Shimadzu Seisakusho Ltd.

Test for blood platelet aggregation capacity:

This test was carried out by using a blood platelet-rich blood plasma prepared to have $30 \times 10^4$ blood platelet per $mm^3$ and ADP of a final concentration of $10^{-5}M$ as an aggregation initiator. The measurement was performed with an automatic blood platelet aggregation capacity tester produced by Kyoto Daiichi Kagakusha and marketed under trademark designation of "Aggricoder PA-3210," under the coditions of 1000 rpm and 37° C.

As described above, the medical instrument in accordance with this invention is a shaped article made of a resin composition comprising 100 parts by weight of vinyl chloride type resin, 10 to 80 parts by weight of a di-n-alkyl ester of phthalic acid possessing the general formula I, and 1 to 18 parts by weight of a stabilizer. Although the plasticizer exudes in an extremely small amount from the resin composition used in the medical instrument, it has a high plasticizing efficiency and, when incorporated in a proportion similar to DOP in the conventional resin composition, imparts flexibility and other desirable properties. Thus, the resin composition can be used safely and advantageously in a wide variety of medical instruments. The resin composition enjoys high permeability to gas. When it is used as the material for the blood bag, it exhibits a very high ability to preserve blood corpuscles. Moreover, this resin composition can be effectively worked (molding, high-frequency sealing, adhesion and sterilization) similarly to the conventional DOP-plasticized vinyl chloride resin. Since this resin composition excels in resistance to cold, it is advantageously used in containers and bags for preserving blood and other fluids in frozen state.

What is claimed is:

1. A medical instrument used for at least one of storage of blood and as a conduit for blood, said medical instrument having at least a part thereof which is in contact with blood when said medical instrument is in service, said part comprising a shaped resin composition, said composition comprising 100 parts by weight of a vinyl chloride type resin,
    from 10 to 80 parts by weight of a di-n-alkyl ester of phthalic acid of the formula

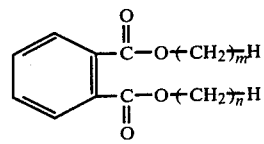

wherein,
    m and n each is an integer of from 8 to 14 and $(m+n)/2$ has a value of from 9 to 14,
    from 1 to 15 parts by weight of an epoxy compound; and
    from 0.01 to 8 parts by weight of a metallic soap;
    the permeability coefficient of said shaped resin composition to carbon dioxide gas is not less than $2.5 \times 10^3$ ml·mm/$m^2$·day·atm (at 30° C.).

2. The medical instrument of claim 1, wherein m and n each is an integer of from 9 to 12.

3. The medical instrument of claim 1, wherein said di-n-alkyl ester of phthalic acid is di-n-decyl phthalate.

4. The medical instrument of claim 1, wherein said at least one part is flexible, and said resin composition comprises 100 parts by weight of said vinyl chloride type resin, 40 to 70 parts by weight of said di-n-alkyl ester of phthalic acid, 5 to 10 parts by weight of said epoxy compound, and 0.05 to 5 parts by weight of the metallic soap.

5. The medical instrument of claim 4, wherein said epoxy compound is an epoxidized vegetagle oil and said metallic soap is a Ca-Zn metallic soap.

6. The medical instrument of claim 1, wherein the instrument is a blood bag.

7. The medical instrument of claim 6, wherein m and n each is an integer of from 9 to 12.

8. The medical instrument of claim 7, wherein said vinyl chloride type resin is polyvinyl chloride having an average polymerization degree of from 700 to 3000.

9. The medical instrument of claim 8, wherein said average polymerization degree is from 1000 to 2400 and wherein said di-n-alkyl ester of phthalic acid is di-n-decyl phthalate.

10. The method of preserving blood comprising storing blood in a blood bag, said blood bag having internal portions which contact the blood, said internal portions comprising a shaped resin composition, said composition comprising 100 parts by weight of a vinyl chloride type resin,
    from 10 to 80 parts by weight of a di-n-alkyl ester of phthalic acid of the formula

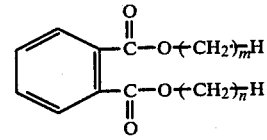

wherein,
    m and n each is an integer of from 8 to 14 and $(m+n)/2$ has a value of from 9 to 14,
    from 1 to 15 parts by weight of an epoxy compound; and
    from 0.01 to 8 parts by weight of a metallic soap;
    the permeability coefficient of said shaped resin composition to carbon dioxide gas is not less than $2.5 \times 10^3$ ml·mm/$m^2$·day·atm (at 30° C.).

11. The process of claim 10, wherein m and n each is an integer of from 9 to 12.

12. The process of claim 10, wherein said di-n-alkyl ester of phthalic acid is di-n-decyl phthalate.

13. The process of claim 10, wherein said at least one part is flexible, and said resin composition comprises 100 parts by weight of said vinyl chloride type resin, 40 to 70 parts by weight of said di-n-alkyl ester of phthalic acid, 5 to 10 parts by weight of said epoxy compound, and 0.05 to 5 parts by weight of the metallic soap.

14. The process of claim 13, wherein said epoxy compound is an epoxidized vegetagle oil and said metallic soap is a Ca-Zn metallic soap.

15. The process of claim 14, wherein m and n is an integer of from 9 to 12.

16. The process of claim 15, said vinyl chloride type resin is polyvinyl chloride having an average polymerization degree of from 700 to 3000.

17. The process of claim 16, wherein said average polymerization degree is from 1000 to 2400 and wherein said di-n-alkyl ester of phthalic acid is di-n-decyl phthalate.

* * * * *

UNITED STATES PATENT AND TRADEMARK OFFICE
CERTIFICATE OF CORRECTION

PATENT NO. : 4,657,542

DATED : April 14, 1987

INVENTOR(S) : Y. OHACHI

It is certified that error appears in the above-identified patent and that said Letters Patent is hereby corrected as shown below:

Column 2, line 19, change "mm.mm/m$^2$" to --ml.mm/m$^2$--.

Column 5, line 30, change "the" (second occurance)
    to --a--.

Column 8, line 41, change "paltelet" to --platelet--.

Column 10, Claim 7 (line 1), change "claim 6" to
    --claim 5--.

Signed and Sealed this

Twenty-third Day of March, 1993

*Attest:*

STEPHEN G. KUNIN

*Attesting Officer*     *Acting Commissioner of Patents and Trademarks*